United States Patent
Glennon et al.

(10) Patent No.: US 6,866,833 B1
(45) Date of Patent: Mar. 15, 2005

(54) SUBSTITUTED THIOUREA COMPLEXING AGENT AND A METHOD FOR EXTRACTING A NOBLE METAL FROM A MATRIX USING THE COMPLEXING AGENT

(75) Inventors: Jeremy Denis Glennon, Carrigaline (IE); Stephen John Harris, deceased, late of Dublin (IE); by Jane Harris, legal representative, Dublin (IE)

(73) Assignee: University College Cork, Cork (IE)

( * ) Notice: Subject to any disclaimer, the term of this patent is extended or adjusted under 35 U.S.C. 154(b) by 0 days.

(21) Appl. No.: 09/890,967

(22) PCT Filed: Feb. 8, 2000

(86) PCT No.: PCT/IE00/00018

§ 371 (c)(1),
(2), (4) Date: Mar. 11, 2002

(87) PCT Pub. No.: WO00/47556

PCT Pub. Date: Aug. 17, 2000

(30) Foreign Application Priority Data

Feb. 8, 1999 (IE) .............................................. S990086

(51) Int. Cl.$^7$ ........................ C22B 11/00; C07C 335/00
(52) U.S. Cl. ............................. 423/22; 423/24; 564/17; 564/26; 564/29
(58) Field of Search ....................... 423/22, 24; 564/17, 564/26, 29

(56) References Cited

U.S. PATENT DOCUMENTS 3,546,344 A * 12/1970 Martin et al. ................ 514/585
4,468,380 A * 8/1984 O'Doherty et al. .......... 424/114
5,021,412 A * 6/1991 Nakaya et al. ........... 415/223.8

FOREIGN PATENT DOCUMENTS

CH      431491    * 8/1967
DE     4016071    * 11/1990

* cited by examiner

*Primary Examiner*—Steven Bos
(74) *Attorney, Agent, or Firm*—Sughrue Mion, PLLC

(57) ABSTRACT

A substituted thiourea having the general formula

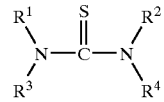

characterized in that each of $R^1$ and $R^2$ independently comprises an alkyl, alkaryl or aryl group or a substituted derivative thereof, and contains at least one fluorine atom, and in that each of $R^3$ and $R^4$ is selected from the group which consists of H, alkyl, alkaryl and aryl and substituted derivatives thereof, including fluorine-containing derivatives. A method for producing the substituted thiourea is disclosed, and a method for extracting a noble metal such as gold from a matrix by treating the matrix with the substituted thiourea is also disclosed.

14 Claims, No Drawings

SUBSTITUTED THIOUREA COMPLEXING AGENT AND A METHOD FOR EXTRACTING A NOBLE METAL FROM A MATRIX USING THE COMPLEXING AGENT

BACKGROUND OF THE INVENTION

This invention relates to a complexing agent and in particular to new fluorinated thiourea complexing agents and fluorinated thiourea complexing agents for use in the extraction of noble metals such as gold, platinum, silver, palladium and rhodium.

Complexing agents are widely employed in the extraction and recovery of metals such as gold, platinum, silver, palladium and rhodium.

For example, gold is a soft yellow metal having a melting point of 1063° C. with the highest ductility and malleability of any element. It is chemically unreactive and is not attacked by oxygen or sulphur but reacts readily with halogens or with solutions containing or generating chlorine such as "aqua regia". Its most common compounds exist in the (I) and (III) oxidation states.

Heretofore, the extraction of gold from one and from other solid phases such as in solid phase extraction has been commonly carried out by using cyanide or thiourea as reagents. In the most commercially important method for gold extraction finely crushed ore is treated with sodium cyanide in the presence of oxygen to give a sodium gold cyanide complex, which is typically absorbed onto activated carbon. The sodium gold cyanide complex can be re-extracted later and reduced to the metal, (H. Schmidbaur, Interdisciplinary Science Reviews, 17 (3), 213, 1992 and A. Sigel and H. Sigel in "Handbook on Metals in Clinical and Analytical Chemistry", Ed. H. G. Seller, 1994 p388) viz:

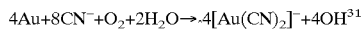

$$4Au + 8CN^- + O_2 + 2H_2O \rightarrow 4[Au(CN)_2]^- + 4OH^{31}$$

However, treatment with sodium cyanide is environmentally unfriendly while the efficiency of the reaction can be poor and variable according to the ore type. Accordingly, other methods of gold and silver extraction have been developed e.g. thiourea-based extraction. Thiourea-based extractions enjoy the advantages of higher leaching efficiency, rapid leaching, adaptation to a variety of refractory ores and reduced toxicity to the environment. Accordingly, thioureation is an attractive procedure for the extraction of both gold and silver.

For example, it has been demonstrated (C. K. Chen, T. N. Lung and C. C. Lung and C. C. Wan, Hydrometallurgy, 5, 207, 1980) that employing $Fe^{3+}$ as oxidant in acid solutions resulted in leaching with thiourea which was ten times faster than leaching with sodium cyanide, viz:

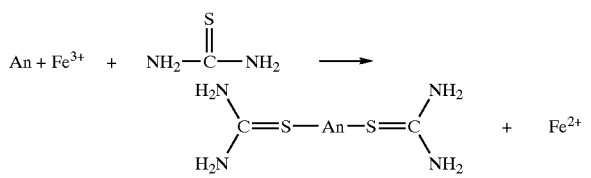

However, excessive consumption of thiourea in the process has limited its industrial application.

Various attempts have been made to reduce thiourea consumption. For example, in order to reduce thiourea consumption in gold extraction it has been suggested (C. C. Kenna, Gold Bull, 24(4), 126, 1991) that the complexing of ferric ions could be utilised in reducing their oxidative power to a level where oxidation of gold still proceeded at an acceptable rate while oxidation (and consumption) of thiourea was greatly reduced.

U.S. Pat. No. 5,126,038 also discloses that alkyl hydroxamic acids or their salts may be used to improve extraction of precious metals, including gold, from sulphide ores in combination with standard sulphide ore collectors such as xanthates, substituted thioureas and the like.

G. Zuo and M. Muhammed, Separation Science and Technology, 25(13–15), 1785, 1990 also describe the synthesis and characterisation of a family of thiourea based reagents for the extraction of Au(III) and Ag(I) ions through complex formation from HCl solutions and also disclose the synthesis of several co-ordinating polymers by grafting thiourea functional groups onto commercial macroporous polystyrene polymer matrices.

In order to avoid the use of thioureas, azacrowns have also been used to facilitate transport of $NaAu(CN)_2$ into an organic phase from an aqueous phase (M. Tromp, M. Burgard, M. J. F. Leroy and M. Prevost, J. of Membrane Science, 38, 295, 1988). In addition, Izatt et al., (R. L. Bruening, B. J. Tarbet, T. E. Krakowiak, M. L. Bruening, R. M. Izaat and J. S. Bradshaw, Anal. Chem., 83(10), 1014, 1991 and R. L. Bruening, B. J. Tarbet, K. E. Krakowiak, R. M. Izatt and J. S. Bradshaw, J. Heterocyclic Chem., 27 347, 1990) have developed silica gel bound thia—macrocycles which have shown high selectivity for Au(III).

Supercritical fluid extraction (SFE) has developed into an attractive alternative to conventional solvent extraction to recover organic compounds from solids in particular. A useful fluid for SFE work is liquid carbon dioxide due to its moderate critical constants ($T_c$=31.1° C., $P_c$=72.8 atm), inertness, ease of availability, low cost and ease of final removal. However, direct extraction of metal ions by supercritical $CO_2$ is very inefficient due to the change neutralisation required and weak solute-solvent interactions.

Supercritical fluid extraction of gold has been described by S. Wang, S. Eishoni and C. M. Wal, Anal. Chem., 67, 919 1995 where Au(III) ions were extracted by bis-triazalocrowns from wet solid matrices using supercritical $CO_2$ modified with methanol. Neutral gold complexes were formed due to the presence of triazalo protons:

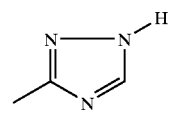

which were soluble in modified SF—$CO_2$. The presence of the triazolo protons was necessary for the extraction of the metal ions to give a neutral metal ion-ligand complex:

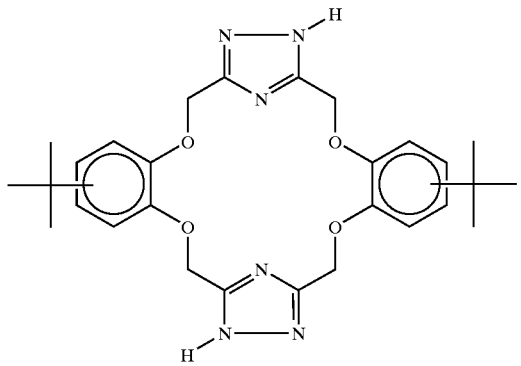

and no extraction was possible without methanol modifier or water in the solid phase. Supercritical $CO_2$ has also been utilised (E. O. Out, Separation Science and Technology 32, 6, 1107, 1997) to elute gold in the form of $NaAu(CN)_2$ previously adsorbed on activated charcoal employing tributylphosphate to facilitate charge neutralisation. However, the presence of water in the solid phase was required for the extraction while are indicated previously the use of cyanide is undesirable for environmental and safety reasons.

SUMMARY OF THE INVENTION

An object of the invention is to overcome the problems of the prior art.

A further object of the invention is to provide a complexing agent or ligand for noble metal (including gold) extraction.

A further object of the invention is to provide a complexing agent or ligand for noble metal (including gold) extraction.

A still further object of the invention is to provide a method for extracting noble metals (including gold) which overcomes the problems of the prior art.

According to the invention there is provided a thiourea having the general formula:

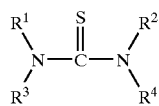

wherein each of $R^1$ and $R^2$ independently comprises an alkyl, alkaryl or aryl group or a substituted derivative thereof, and contains at least one fluorine atom, and wherein each of $R^3$ and $R^4$ is selected from the group which consists of H, alkyl, alkaryl and aryl, and substituted derivatives thereof, including fluorine-containing derivatives. In one aspect of the invention $R^3$ and $R^4$ are selected from the group consisting of alkyl, alkaryl and aryl, and substituted derivatives thereof including fluorine-containing derivatives. The fluorinated derivatives of the invention are extremely useful for analytical assays for the determination of gold levels, and for gold recovery, as well as for determination of platinum, silver, palladium and rhodium levels and for their recovery.

Preferably, $R^1$ comprises

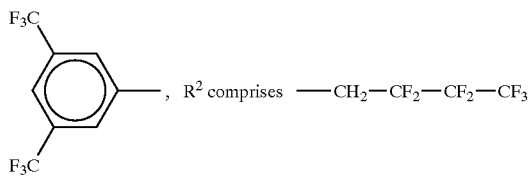, $R^2$ comprises —$CH_2$—$CF_2$—$CF_2$—$CF_3$ $R^3$ comprises H and $R^4$ comprises H.

Alternatively, $R^1$ comprises

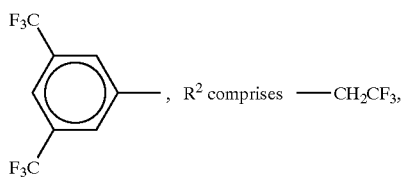, $R^2$ comprises —$CH_2CF_3$, $R^3$ comprises H and $R^4$ comprises H.

The invention also extends to a method of producing a fluorinated thiourea comprising reacting a compound of general formula

with a compound of general formula

where both $R^1$ and $R^2$ contain fluorine.

The invention also relates to a method for extracting gold from a matrix comprising treating the matrix with a thiourea having the general formula

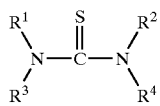

where $R^1$ and $R^2$ comprise a fluorine containing alkyl, alkaryl, aryl or substituted derivatives thereof and $R^3$ and $R^4$ are selected from the group comprising H, alkyl, aryl or substituted derivatives thereof and subjecting the matrix to supercritical fluid extraction (SFE).

Preferably, the supercritical fluid used in the extraction comprises liquid carbon dioxide.

Preferably, $R^1$ comprises

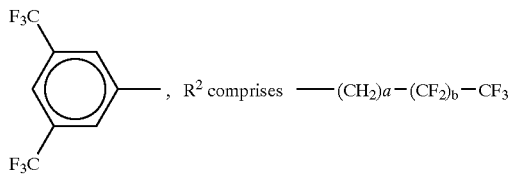, $R^2$ comprises —$(CH_2)_a$—$(CF_2)_b$—$CF_3$ $R^3$ comprises H and $R^4$ comprises H where $a \geq 1$ and $b=0-6$.

In one embodiment of the invention the gold is extracted in the presence of an oxidant. Suitably, the oxidant comprises Fe (III) ions.

Advantageously, b>3, i.e. b=4, 5 or 6.

The invention also extends to the use of a fluorinated thiourea of the general formula

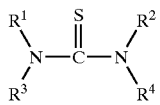

where $R^1$ and $R^2$ comprise a fluorine containing alkyl, alkaryl, aryl or substituted derivatives thereof and $R^3$ and $R^4$ are selected from the group comprising H, alkyl, aryl, alkaryl or substituted derivatives thereof in the extraction of a noble metal, including gold, platinum, silver, palladium and rhodium from a matrix.

Surprisingly, it has been found that fluorinated thioureas of the general formula:

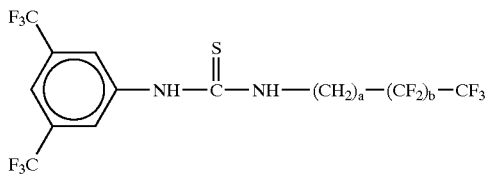

wherein $a \geq 1$ and $b=0-6$ efficiently extract Au(I) and Au(III) from a solid matrix in unmodified supercritical $CO_2$ and furthermore may extract gold from a solid containing gold in its elemental form in the presence of an oxidant. Fe(III) ions are particularly suitable as oxidants. The addition of modifiers or protons is not required and extraction can be carried out using fluorinated thioureas alone.

In contradistinction, thiourea itself does not form a neutral complex with gold. It forms Au $[SC(NH_2)_2]_2^+$.

In a preferred embodiment of the invention b>3, i.e. b=4, 5 or 6.

The fluorinated thioureas of the invention have a high solubility in supercritical $CO_2$ and are extremely efficient at solubilising and carrying noble metals such as gold for the purposes of extraction, recovery, deposition or impregnation.

The fluorinated thioureas can be synthesised in a simple one-step process by the reaction of:

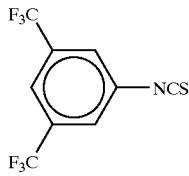

with the appropriate amine $NH_2CH_2(CF_2)_bCF_3$ where b=0 or 2 to 6 in a room temperature (exothermic) reaction and recrystallisation from petroleum ether (100–120) to give colourless products in 62 to 81% yields.

The compositions of the invention can therefore be formed by the simple reaction of:

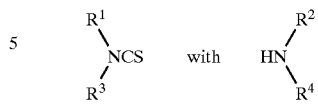

where both $R^1$ and $R^2$ contain fluorine.

DETAILED DESCRIPTION OF THE INVENTION

Various embodiments of the invention will now be described by way of Example only, having regard to the following data and examples.

COMPARATIVE EXAMPLES (a)

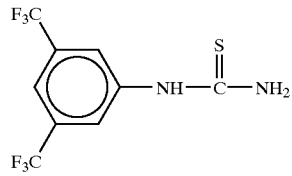

The aforementioned fluorinated thiourea is known from the prior art and is commercially available from FLUOROCHEM.

(b)

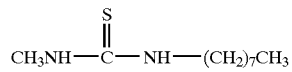

In a round bottom flask 6.46 g (0.05 mole) of octyl-1-amine was added to 3.65 g (0.05 mole) melted methyl isothiocyanate, with stirring, under nitrogen in an ice bath. A rapid exothermic reaction ensued and the reaction was allowed to reach room temperature overnight. The colourless solid product (10.02 g, 99% yield) was recrystallised from 100–120° C. petroleum ether to give 9.99 g of N-methyl,N'-octyl thiourea as a white solid. Note: The oil, which settles out on cooling, solidifies on standing, yield 99%. Elemental Analysis for $C_{10}H_{22}N_2S$ Calculated: C: 59.36, H; 10.96, N; 13.84, S; 15.84% Found: C: 59.60, H 10.99, N; 13.50, S; 16.11%

(c)

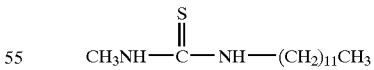

In a round bottom flask 9.27 g (0.05 mole) dodecyl-1-amine was added to 3.65 g (0.05 mole) of melted methylisothiocyanate with stirring under nitrogen. A rapid exothermic reaction ensued and the reaction mixture was allowed to reach room temperature overnight. The colorless solid product 12.45 g (96% yield) was recrystallised from 100–120° C. petroleum ether to give 12.27 g (95% yield) of N-methyl, N'-dodecyl thiourea as white crystals. Elemental Analysis for $C_{14}H_{30}N_2S$ Calculated: C: 65.05, H; 11.70, N; 10.84, S; 12.40% Found: C: 64.90, H; 11.67, N; 11.10, S; 12.78%

Example 1

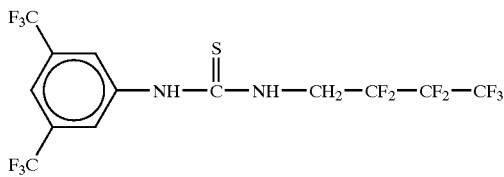

To 0.518 g (0.0026 mole) 1H, 1H-heptafluorobutylamine (Fluorochem (Trade Mark) Product FO4396) in a round bottom flask was added 0.705 g (0.0026 mole) 3,5-di(trifluoromethyl) phenylisothiocyanate (Fluorochem (Trade Mark) Product F03115B). After stirring for one minute the miscible liquids solidified to a colourless solid in an exothemic reaction. After the reaction mixture had cooled it was allowed to stand for 1 hour at room temperature and the product was recrystallised from petroleum ether (100–120) to give 0.972 g of pure product (80% yield) as colourless crystals, mp 130–132° C.

Elemental Analysis for $C_{13}H_7N_2SF_{13}$: Calculated: C: 33.20, H; 1.50, N; 5.96, Found C: 33.05, H; 1.49, N; 8.12%

Example 2

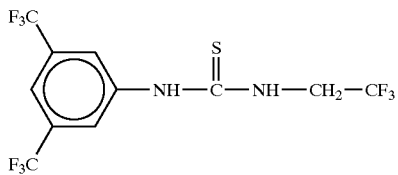

To 0.705 g (0.0026 mole) 3,5-di(trifluoromethyl)-phenylisothiocyanate in a round bottom flask cooled in an ice bath, with stirring under nitrogen, was added 0.281 g (0.00283 mole) trifluoroethyl amine (Aldrich (Trade Mark) produce 26,904-2). After a short period an exothermic reaction occurred to give a colourless solid. The reaction mixture was then allowed to warm to room temperature and was left for 1 hour under a stream of dry nitrogen to remove excess volatile amine (bp 36° C.). The solid was recrystallised from petroleum ether (100–120) to give a pure product as fluffy colourless crystals 0.80 g (62% yield), m.p. 133–136° C. Elemental Analysis for $C_{11}H_7N_2SF_2$: Calculated: C: 35.64, H; 2.04, N; 7.55, Found C: 35.94, H; 2.20, N; 7.73%

Example 3(a)

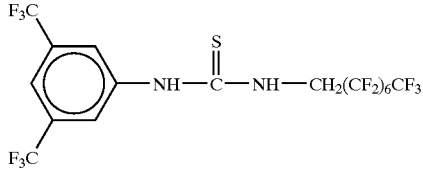

To 3.28 (0.0121 mole) 3,5-di(trifluoromethyl)-phenylisothiocyanate in a round bottom flask was added 4.82 g (0.0121 mole) 1H, 1H-perfluoro-octylamine Lancaster (Trade Mark) product 16845 with stirring. An exothermic reaction rapidly ensued and after cooling to room temperature was allowed to remain for 2 hours. The white solid product was recrystallised from 100–120° C. petroleum ether to give 6.50 g pure product (81% yield) as a colourless crystalline solid. Elemental Analysis: $C_{17}H_7N_2SF_2$: Calculated: C: 30.46, H; 1.05, N; 4.18; Found: C:30.60, H; 1.16, N; 4.40%

Example 3(b)

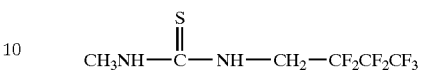

In a round bottomed flask 5.92 g (0.03 mole) of 1H, 1H-heptafluorobutyl amine was added to 2.18 g (0.30 mole) of melted methyl-isothiocyanate with stirring under nitrogen. An exothermic reaction ensued and the reaction mixture was allowed to reach room temperature overnight. The colourless product 8.10 g (100% yield) was recrystallised from 100–120° C. petroleum ether to give N-methyl, N'-heptafluorobutyl thiourea, 6.91 g, as a white solid in 85% yield. Elemental Analysis for $C_8H_7N_2SF_7$ Calculated: C: 26.48, H; 2.59, N; 10.29, S; 11.78% Found: C: 26.71, H; 2.57, N; 10.50, S; 12.25%

Example 4

The solubility of the ligand of the comparative Examples (a)–(c) in supercritical $CO_2$ was compared with the solubilities of the ligands of Examples 1 and 2 and 3 in supercritical $CO_2$.

In each case, a weighed amount of the ligand of the respective comparative Example of approximately 60 mg was placed in a glass tube (2 cm×0.5 cm i.d.) and plugged with glass wool at both ends. The glass tube was placed inside the extraction vessel and statically extracted for 30 minutes. The inlet valve for SF—$CO_2$ was then closed and the outlet valve opened into a collecting solution. The loss of weight of the glass tube after SFE corresponded to the solubility of the ligand in 2.2 ml 100% SF—$CO_2$. The procedure was carried out at 60° C. and two different pressures namely 200 and 300 atmospheres.

In all three cases, most of the ligand appeared to remain in the glass tube indicating poor solubility in SF—$CO_2$.

Solubility of the Ligand of Example 1 in Supercritical $CO_2$:

The procedure outlined above in Example 4 was repeated for the ligand of Example 1. This time none of the ligand remained in the glass tube, indicating excellent solubility in SF—$CO_2$ at both pressures.

Solubility of the Ligand of Example 2 in Supercritical $CO_2$:

The procedure outlined above in Example 4 was repeated for the ligand of Example 2. Again, none of the ligand remained in the glass tube, indicating excellent solubility in SF—$CO_2$ at both pressures.

Solubility of the Ligand of Example 3(a) in Supercritical $CO_2$:

The procedure outlined above in Example 4 was repeated for the ligand of Example 3(a). Again, none of the ligand remained in the glass tube, indicating excellent solubility in SF—$CO_2$ at both pressures.

Solubility of the Ligand of Example 3(b) in Supercritical $CO_2$:

The procedure outlined above in Example 4 was repeated for the ligand of Example 3(b). Again, none of the ligand remained in the glass tube, indicating excellent solubility in SF—$CO_2$ at both pressures. Larger amounts of ligand 3(b) were used and solubilities in excess of 0.7 M were thus found at both pressures. Thus the newly synthesised thioureas were found to be highly soluble in supercritical $CO_2$ compared to the fluorinated and two non-fluorinated thioureas of the Comparative Examples (a)–(c).

A number of experiments were carried out to demonstrate the extraction efficiencies of the fluorinated thioureas of the invention.

Example 5(a) (Comparative)

Supercritical Fluid Extraction of Au(III) as $AuCl_4^-$ using the Compound of the Comparative Example (a)

Gold Au(III) extraction by the ligand of the comparative Example (a) was investigated employing a BDH Gold (III) standard containing 1000 ppm Au(III) (aqueous $AuCl_4^-$). Thus 60 μl of solution Au(III) containing $3.05 \times 10^{-7}$ moles Au(III) was applied to a 3 cm diameter filter paper. The filter paper was allowed to dry and then placed in a glass tube (2 cm×0.5 cm i.d.), plugged with glass wool at both ends. 20 mg of ligand of the comparative Example (a) (in excess of over 200 fold over Au(III) level) was then placed in the same glass tube and plugged with glass wool. The temperature of the extraction vessel was then set at 60° C. and the pressure was varied as indicated in Table 1.

The extraction vessel was statically extracted for 20 minutes and then dynamically extracted into a collecting solvent of 4 ml methanol for 15 minutes (0.8 ml $CO_2$/minute flow rate). The methanol solution was then made up to 10 ml using additional methanol. Levels of gold in solution were then determined by atomic absorption spectroscopy. The procedure was carried out at different pressures from 200–400 atm. The following extraction percentages were obtained:

TABLE 1

| Pressure SF—$CO_2$ (atm) | Atomic Absorption (A.U.)* | Extraction (%) |
| --- | --- | --- |
| 200 | 0.000 | 0 |
| 250 | 0.000 | 0 |
| 300 | 0.001 | ~0.0 |
| 350 | 0.000 | 0 |
| 400 | 0.024 | 6.7 |

*The % extraction is calculated with reference to the Atomic Absorption reading obtained for 10 ml of collecting solution spiked directly with 60 μl of the 1000 ppm Au(III) standard. (For example for the data presented in Table 1 a standard of 60 μg/10 ml = 6 ppm Au, gave an absorption value of 0.359, representing 100% extraction. Note: such recordings of standard values were carried out alongside the sample analysed on the same day.)

400 atm was the only pressure of SF—$CO_2$ to give detectable Au(III) extraction. In all runs most of the ligand appeared to remain in the glass tube indicating poor solubility in SF—$CO_2$.

Example 5(b) (Comparative)

Supercritical Fluid Extraction of Au(III) as $AuCl_4^-$ using the Compound of the Comparative Example (b)

The procedure of Example 5(a) was repeated for Comparative Example (b) to give 3.2% gold extraction at 250 atmospheres and 2.0% at 450 atmospheres pressure. Most of the ligand appeared to remain in the glass tube after all runs indicating poor solubility in SF—$CO_2$.

Example 5(c) (Comparative)

Supercritical Fluid Extraction of Au(III) as $AuCl_4^-$ using the Compound of the Comparative Example (c)

The procedure of Example 5(a) was repeated for Comparative Example (c) to give 2.6% gold extraction at 250 atmospheres and 1.3% at 450 atmospheres pressure. Most of the ligand appeared to remain in the glass tube after all runs indicating poor solubility in SF—$CO_2$.

Example 6 (Comparative)

The procedure in Example 5(a) was repeated except the temperature of the extraction procedure was varied from 60–120° C., while maintaining the pressure of the extractor at 400 atm. The following results were obtained:

TABLE 2

| Temperature (° C.) | Atomic Absorption (A.U.)* | Extraction (%) |
| --- | --- | --- |
| 60 | 0.027 | 8.8 |
| 80 | 0.002 | 0.7 |
| 100 | 0.006 | 2.0 |
| 120 | 0.005 | 1.6 |

*A standard of 6 ppm Au, gave an absorption value of 0.305 = 100%

The % extraction of gold remained low.

Example 7

The procedure in Example 6 was repeated with the ligand from Example 1 being used in place of the ligand of the Comparative Example (a). The following % extraction values were obtained at differing pressures for extraction of Au(III):

TABLE 3

| Pressure SF—$CO_2$ (atm) | Extraction (%) |
| --- | --- |
| 200 | 61.2 |
| 250 | 92.7 |
| 300 | 83.7 |
| 350 | 75.3 |
| 400 | 78.1 |

Percentage extraction with the ligand of the invention was therefore excellent at 92.7% compared with the poor extraction (<10%) with the ligands of the comparative Examples.

Example 8

Reduction of Au(III) to Au(O) was accomplished by treatment with hydroxylamine hydrochloride followed by sodium hydroxide.

The procedure in Example 7 was repeated except the conditions were altered to 60° C. at 250 atm. The 60 μl of $AuCl_4^-$ was replaced by 60 μl of a well mixed even suspension of Au(O) applied to the filter paper which was allowed to dry to give a black-blue colour.

The collected methanol solutions, made up to 10 ml as before, were analysed by Atomic Absorption Spectroscopy as before, giving the following % extraction values:

TABLE 4

| Pressure SF—$CO_2$ (atm) | Atomic Absorption (A.U)* | Extraction (%) |
| --- | --- | --- |
| 200 | 0.001 | ~0.0 |
| 250 | 0.002 | ~0.0 |
| 300 | 0.0001 | ~0.0 |
| 350 | 0.002 | ~0.0 |
| 400 | 0.002 | ~0.0 |

Accordingly, the ligand of Example 1 did not extract Au(O). Moreover, at the end of the runs the blue-black colour of Au(O) remained on the filter paper and no ligand remained in the tube. However, as described further below the gold could be extracted following oxidation of Au(O) to either Au(I) or Au(II).

Example 9

The procedure in Example 8 was repeated but 40 mg of solid Au(O) was used in place of the Au(O) suspension deposited on the filter paper to give an identical result to Example 8.

Example 10

The procedure of Example 9 was repeated utilising 20 mg of the ligand Example 1 except 11.2 mg of solid Au(O) was used and on two occasions the Au(O) was first oxidised to Au(I) by spiking 60 µl of Fe(III) (1000 ppm stock solution) onto the solid Au(O) directly and then allowed to dry. In the case where Fe(III) had been added when the collected methanol solution (as usual made up to 10 ml) was analysed by atomic absorption a large signal was obtained (0.252) and (0.253) indicating extraction of Au(I). Fe(III) was the limiting reagent as:

$$Fe(III)+Au(O) \rightarrow Fe(II)+Au(I)$$

and therefore 60 µl 1000 ppm Fe(III) (1.075 µmole) is equivalent to 212 µl of 1000 ppm Au(I) (0.2 mg Au).

Table 5 below outlines the results obtained following application of Fe(III):

TABLE 5

| Sample | Atomic Absorption (A.U.)* | Extraction (%) |
|---|---|---|
| 11.2 mg Au(O) + 20 mg ligand of Example 1 | 0.001 | 0 |
| 11.2 mg Au(O) + 60 µl Fe(III) + 20 mg ligand of Example 1 | 0.252 | 20.0 |
| 11.2 mg Au(O) + 60 µl Fe(III) + 20 mg ligand of Example 1 | 0.253 | 20.0 |

A 212 µl aliquot of 1000 pp, Au(III) standard solution gave an absorption value of 1.263=100%.

Accordingly, Au(O) has been successfully oxidised by Fe(III) to give Au(I) which has been extracted with the fluorinated ligand of the invention. That only 20% of the theoretically freed gold (by Fe) was finally detected by atomic absorption is not surprising in view of the fact that the Fe(III) was applied as a 1000 ppm aqueous nitrate solution to the solid Au(O) on the filter paper without thorough mixing. Nevertheless, the method can be employed successfully as a qualitative test for Au(O).

Example 11

The procedure of Example 7 was repeated employing the ligand of Example 2 in place of the ligand of Example 1 and utilising 50 µl Au(III) standard solution in place of 60 µl to give the following % extraction results at differing pressures of SF—$CO_2$ at 60° C.

TABLE 6

| Atmosphere SF—$CO_2$ | Extraction (%) |
|---|---|
| 200 | 41 |
| 250 | 51 |
| 300 | 22 |
| 400 | 14 |

Example 12

The procedure of Example 11 was repeated except Au(III) standard was replaced by 5.7 mg solid Au(O) and extraction was determined under previously optimised conditions 60° C./250 atm SF—$CO_2$. Table 7 summarises the results:

TABLE 7

| Sample | Extraction (%) |
|---|---|
| Au(O) + ligand | ~3 |

Example 13

Above Example 12 was repeated except that 30 µl 1000 ppm Fe(III) standard (aqueous nitrate) was spiked onto the Au(O) prior to extraction with SF—$CO_2$ (250 atm/60° C.). Table 8 below summarises the results obtained.

TABLE 8

| Sample | Extraction (%) |
|---|---|
| Au(O) + 30 µl Fe(III) + 20 mg ligand | 57 |

The above percentage is based on the Fe(III) oxidisable quality of gold i.e. Fe(III) is the limiting reagent.

57% of the "freed" gold Au(I) was therefore extracted with the fluorinated ligand of the invention.

Advantages of the invention include (but are not limited to) the following:

The linear fluorinated thioureas of the invention therefore have the unexpected property of extracting Au(III) in supercritical $CO_2$. In addition Au(I) may be extracted from Au(O) (in its elemental state) by prior treatment with Fe(III).

The complexing agents and extraction methods of the invention are highly efficient and do not require the use of cyanides. In addition, the fluorinated thioureas of the invention facilitate the extraction of noble metals (including gold, platinum, silver, palladium and rhodium) without excessive thiourea consumption.

Moreover, extraction of noble metals (including gold, platinum, silver, palladium and rhodium) using fluorinated thioureas and supercritical fluid can be effected without requiring the addition of modifiers, protons and the like.

The invention is not limited to the embodiments herein described which may be varied in construction and detail.

What is claimed is:

1. A substituted thiourea having the general formula

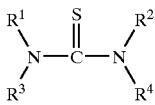

wherein $R^1$ comprises an alkyl, alkaryl or aryl group or a substituted derivative thereof, and contains at least one fluorine atom, $R^2$ is —$CH_2$—$CF_2$—$CF_2$—$CF_3$, and each of $R^3$ and $R^4$ is selected from the group consisting of H, alkyl, alkrayl, aryl, substituted derivatives of H, alkyl, alkaryl or aryl, and fluorine-containing derivatives of H, alkyl, alkaryl or aryl.

2. A thiourea according to claim 1 wherein $R^1$ is

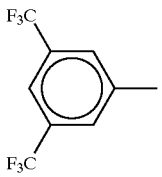

3. A thiourea according to claim 1 wherein $R^3$ is H.
4. A thiourea according to claim 1 wherein $R^4$ is H.
5. A thiourea according to claim 2 wherein the substituted thiourea is of the formula

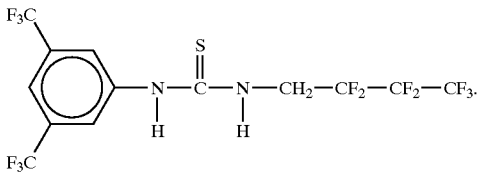

6. A method for extracting a noble metal from a matrix, the method comprising the steps of treating the matrix with a substituted thiourea having the general formula

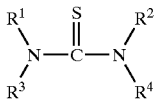

wherein $R^1$ and $R^2$ independently comprise an alkyl, alkaryl or aryl group or a substituted derivative thereof, and contain at least one fluorine atom, and each of $R^3$ and $R^4$ is selected from the group consisting of H, alkyl, alkaryl, aryl, substituted derivatives of H, alkyl, alkaryl or aryl, and fluorine-containing derivatives of H, alkyl, alkaryl or aryl, and subjecting the thus treated matrix to supercritical fluid extraction.

7. A method according to claim 6 wherein the noble metal is gold, platinum, silver, palladium or rhodium.

8. A method according to claim 6 wherein the supercritical fluid is supercritical carbon dioxide.

9. A method according to claim 6 wherein the treatment with substituted thiourea is performed in the presence of an oxidant.

10. A method according to claim 9 wherein the oxidant comprises ferric ($Fe^{III}$) ions.

11. A method according to claim 6 wherein the treatment and extraction are carried out at room temperature and are followed by recrystallisation of the product from petroleum ether at a temperature in the range of 100° C. to 120° C.

12. A substituted thiourea having the general formula

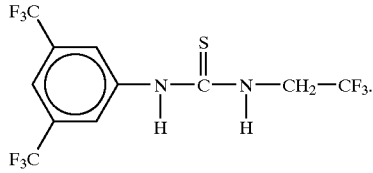

13. A method of extracting gold, platinum, silver, palladium or rhodium from a matrix comprising:
treating the matrix with a substituted thiourea, and
subjecting the treated matrix to supercritical fluid extraction, wherein the substituted thiourea has the general formula

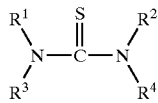

wherein $R^1$ and $R^2$ independently comprise an alkyl, alkaryl or aryl group or a substituted derivative thereof, and contain at least one fluorine atom, and each of $R^3$ and $R^4$ is selected from the group consisting of H, alkyl, alkaryl, aryl, substituted derivatives of H, alkyl, alkaryl or aryl, and fluorine-containing derivatives of H, alkyl, alkaryl or aryl.

14. A method of solubilising and carrying noble metals for deposition or impregnation thereof, comprising:
treating a matrix containing noble metals with a substituted thiourea, and
subjecting the treated matrix to supercritical fluid extraction, wherein the substituted thiourea has the general formula

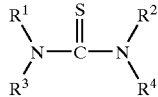

wherein $R^1$ and $R^2$ independently comprise an alkyl, alkaryl or aryl group or a substituted derivative thereof, and contain at least one fluorine atom, and each of $R^3$ and $R^4$ is selected from the group consisting of H, alkyl, alkaryl, aryl, substituted derivatives of H, alkyl, alkaryl or aryl, and fluorine-containing derivatives of H, alkyl, alkaryl or aryl.

* * * * *